United States Patent [19]
Sauter

[11] 4,060,899
[45] Dec. 6, 1977

[54] DOWEL PIN WITH SOCKET FOR THE MANUFACTURE OF DOWEL MODELS IN DENTAL TECHNOLOGY

[76] Inventor: Richard Sauter, Richard Stocker St. 15, D7707 Engen, Germany

[21] Appl. No.: 687,210

[22] Filed: May 17, 1976

[30] Foreign Application Priority Data

May 15, 1975 Germany .............................. 2521573

[51] Int. Cl.² ............................................. A61C 13/00
[52] U.S. Cl. ......................................................... 32/11
[58] Field of Search ................................... 32/11, 40 R

[56] References Cited
U.S. PATENT DOCUMENTS

3,153,283  10/1964  Weissman ............................ 32/40 R
3,518,761  7/1970  Susman et al. ............................ 32/11

*Primary Examiner*—Robert Peshock
*Attorney, Agent, or Firm*—Holman & Stern

[57] ABSTRACT

A dowel pin (stump-form pin) and casing for making crowns and the like wherein the pin is cylindrical having a stump form portion with roughened surface and a pin shaft portion. Anti-rotation means are provided by a milled secant-area being removed from either the end of the pin shaft or a collar head near the retention portion. The casing has a complimentary secant-area projection. The casing can be either rectangular or circular in cross-section and has at least one annular groove for firm anchoring. The casing may also have a roughened surface.

12 Claims, 7 Drawing Figures

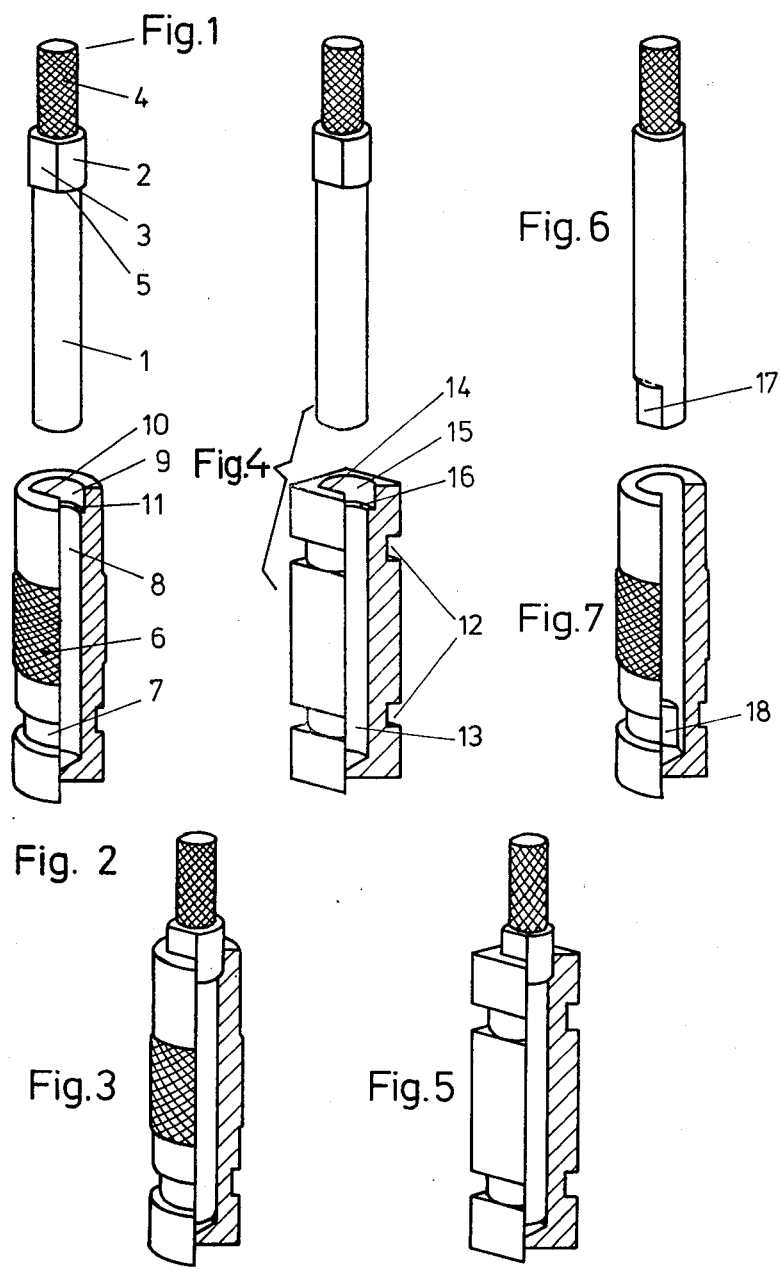

DOWEL PIN WITH SOCKET FOR THE MANUFACTURE OF DOWEL MODELS IN DENTAL TECHNOLOGY

Stump-form pins (dowel pins) are used in dental laboratories for the purpose of inserting the stump forms of the teeth of patients, which have been produced through a multitude of molds, into the a casting of the jaw of the patient for whom crowns and the like are being prepared. The stump form corresponds with the respective tooth-stump in the mouth of the patient. Since the stump-form is inserted into the of the jaw, and can again be removed therefrom, it becomes possible in the dental laboratory to form the crown or the like which is to be placed on the tooth stump and to adapt same in its shape to the adjacent teeth by a repeated inserting into the jaw-model. However, only the crown which has been shaped on the stump-form will be mounted in the mouth of a patient.

Prior art stump-form pins and casings are provided with a roughened retention portion for fastening the stump-form and the conical pin-shaft (U.S. Pat. No. 3,518,761). A pin-shaft having a conical outer surface is disadvantage when it is manufactured if it has a square cross-section. The difficulties lead to a substantial increase in production costs. Additionally, such types of stump-form pins can not be inserted evenly into the plaster cast. Furthermore, the plaster is worn away during the repeated inserting and removing which results in further imprecision.

It is therefore the scope of the instant invention to provide the stump-form pin, and the associated casing, with a form which enables it to be economically manufactured in an automatic working process of a large number of pieces. Additionally, the pins are intended to be selectively replaceable by means of the use of casings which are adapted thereto.

For solving this problem, there is proposed a stump-form pin with a plug-in casing with is provided at one end with a retention section which has its upper surface area roughened and is preferably of cylindrical shape. Adjacent to the retention end, in axial direction, a collar head may be provided with a diameter which is larger than that of the retention section. pin shaft is adjacent to the collar head, and a plug-in casing to be embedded into the plaster impression is provided. the plug-in casing has an axial hole; the form of which is adapted to the outer form of the pin shaft. The pin shaft is of cylindrical shape and the axial hole of the casing is preferably a cylindrical borehole the end of the pin shaft which is remote from the retention section, or on the collar head, a milled secant area is provided, and at the lower end of the cylindrical borehole or in a recess which is provided at the upper end of the casing for receiving the collar-head, for securing the pin inserted into the casing against rotation around its axis, there is provided a projection complementary to the milled secant area, is provided. The outer surface of the casing has at least one coaxial annular groove toward with respect to the axis.

One recognizes that all sections of stump-form pin and casing are cylindrical. They can thus be manufactured simply on automatic machines in a great number and extremely low in cost. Anti-pin rotation areas are simply those sections, which serve for bolting of the pin and casing together to present rotation. These sections are formed as secant areas tangential to the rotation axis and can therefore easily be obtained by means of milling. One obtains a precise seating of the pin in the casing which remains rotation-free even after repeated removal. Additionally, if is well-anchored in the plaster impression by means of the annular groove in the outer periphery of the casing.

The manufacture of such a pin and casing is simplified further when the casing is cylindrical in cross-section and therewith has also a cylindrical outer surface, whose production may also easily be incorporated into the automated manufacturing process. An even more improved anchoring of the casing in the plaster impression is obtained when the casing is rectangular in cross-section. In this case, one suitably starts with a rectangular base material in the manufacture of the casings so that during the manufacturing process itself only rotation areas must be formed. A further improvement of anchoring the casing in the plaster impression results in case where the casing is provided with a roughened annular area at its outer periphery.

Brass is considered the best known material for stump-form pin and casing, and is best suitable.

The invention is exemplified in the drawings, wherein:

FIG. 1 shows a stump-form pin with a collar-head;

FIG. 2 is a partial front-elevational view showing in cross-section a circular casing adapted to the pin of FIG. 1;

FIG. 3 is a partial front-elevational view showing in cross-section the pin of FIG. 1 inserted into the casing according to FIG. 2;

FIG. 4 is a partial front-elevational view of a square casing for receiving the pin of FIG. 1;

FIG. 5 is a partial front-elevational view of a pin according to FIG. 1 inserted into the casing according to FIG. 4;

FIG. 6 illustrates an embodiment of a stump-form pin without a collar head; and

FIG. 7 shows a casing being circular in cross-section in a form adapted to the pin of FIG. 6.

FIG. 1 shows stump-form pins and casings with a cylindrical pin shaft 1 adjacent to which, in axial direction, is a collar head 2 having an enlarged diameter. Also the collar head 2 is substantially cylindrical in shape. In one fractional area, however, there is formed a secant-area 3 by means of milling, along an annular secant, the importance of which being explained hereinbelow. Adjacent to the collar head 2 is a retention section 4, which is aligned in its axis with the pin shaft 1 and collar head 2. It is of cylindrical shape and has a roughened surface for an improved anchoring in the stump-form. The diameter of the retention section 4 is smaller than that of the collar head 2 and suitably also smaller than the diameter of the pin shaft 1.

FIG. 2 shows a casing, adapted to the pin of FIG. 1. This casing is produced from a cylindrical finish material. In a given case, the cylindrical outer upper surface is manufactured first. The cylindrical outer upper surface of the casing according to FIG. 2 is provided with an annular area 6 which is roughened. Further, at the foot, namely near one end of the casing, there is an annular groove 7 milled thereinto. Inside, the casing is provided with a cylindrical borehole 8 in axial direction, which is in the form of a blind hole.

At the upper end of the casing, which forms the opening for the insertion of the pin shaft 1, there is provided a groove 9 for the purpose of enlarging the diameter in comparison to the diameter of the cylindrical borehole 8. Herein, there is additionally a projection 10 protruding from the annular wall of the groove 9 inwardly, which projection corresponds with the secant-area 3 of the collar head 2 of the pin. Thus an insertion of the pin can only be accomplished with the stump-form pin in the correct position and in an inserted condition secures the same with regard to rotation around the axis. When in an inserted condition, the shoulder 5 comes to rest with the bottom portion of the collar head 2 resting on the reduced section 11 which forms on the bottom of groove 9 in transition to the cylindrical borehole 8.

From FIG. 3, it can be easily seen how the pin, with its long pin shaft 1, is inserted into the cylindrical borehole 8 and is secured therein.

FIG. 4 illustrates a different embodiment of the casing. The casing is rectangular and is provided with two annular grooves 12 for anchoring in the plaster impression, since a roughened annular area 6 cannot easily be provided in this case. In general, the cylindrical borehole 13, the projection 14, the groove 15, and the reduced section 16 correspond with the respective sections in the embodiment of the casing according to FIG. 2. The casing of FIG. 4 is to be utilized in connection with the pin of FIG. 1, as indicated by the pin drawn thereabove.

FIG. 5 shows a pin according to FIG. 1 and a casing according to FIG. 4 in an assembled condition.

FIG. 6 shows another embodiment of the pin in which no collar head is provided. The secant-area at the lower end portion of the long pin shaft 1 herein is therefore formed as secant-area 17 by means of milling. To secure the inserted pin against rotations, there is provided a projection 18 at the lower end portion of the blind hole in the casing according to FIG. 7. In general, the secant-areas 17 and the projection 18 function in cooperation, like the secant-areas 3 and the projections 10 or 14 in the embodiments of FIGS. 1 to 5. One can also recognize that by means of the structure of the secant-areas 17 and the projection 18 in the embodiment of FIGS. 6 and 7 there is guaranteed a constant depth-stop which in the embodiments of FIGS. 1 to 5 is obtained by means of the adaption to each other of the depth of the dead hole and the length of the pin shaft 1. It can furthermore be clearly seen from FIG. 6 that the retention portion 4 has a smaller diameter than the pin shaft 1.

What I claim is:

1. A stump-form pin with plug-in casing for manufacturing stump-forms in dental technology comprising:
   an elongated cylindrical pin having opposite ends and a longitudinally extending axis, said pin having three portions along said axis, the first portion being a retention portion at one end of said pin having a roughened surface, the second portion being a cylindrical collar portion having a diameter larger than said retention portion and a secant-area segment removed; the third portion being a pin shaft portion forming the other end of said pin, said pin shaft portion having a diameter smaller than that of said collar portion; and
   a casing for receiving said pin and adapted to be embedded into a plaster-impression, said casing having a cylindrical bore along a longitudinally extending axis, said bore having two portions and a dead end, the first portion of said bore having said dead end and a diameter approximately the same as the diameter of said pin shaft portion of said pin and the second portion of said bore being approximately the same diameter as the diameter of said collar portion of said pin and having an inward secant-area projection complementing the secant-area segment removed from said collar portion for the purpose of securing the pin against axial rotation when said pin is inserted into said casing, said casing having at least one annular groove in its outer surface coaxially with said axis of said casing.

2. The device according to claim 1, wherein said casing has a cylindrical cross-section.

3. The device according to claim 1, wherein said casing has a rectangular cross-section.

4. The device according to claim 3, wherein said casing is provided on its outer area with an annular area which has a roughened surface.

5. The device according to claim 1, wherein said pin and said casing are manufactured of brass.

6. The device according to claim 2, wherein said casing is provided on its outer area with an annular area which has a roughened surface.

7. The device according to claim 3, wherein said pin and said casing are manufactured of brass.

8. A stump-form with plug-in casing for manufacturing stump-forms in dental technology comprising:
   an elongated cylindrical pin having opposite ends and a longitudinally extending axis, said pin having two portions, the first portion being a retention portion at one end of said pin having a roughened surface and the second surface being a pin shaft portion having a diameter larger than said retention portion, said pin having a secant-area segment removed from the other end; and
   a casing for receiving said pin and adapted to be embedded into a plaster-impression, said casing having a cylindrical bore along a longitudinally extending axis with a dead end,
   said bore being approximately the same diameter as said pin shaft portion and having an inward secant-area projection at said dead end of said bore complementing said secant-area segment removed from said pin for the purpose of securing the pin against axial rotation when said pin is inserted into said casing, said casing having at least one annular groove in its outer surface coaxially with said axis of said casing.

9. The device according to claim 8, wherein said casing has a cylindrical cross-section.

10. The device according to claim 8, wherein said casing has a rectangular cross-section.

11. The device according to claim 10, wherein said casing is provided on its outer area with an annular area which has a roughened surface.

12. The device according to claim 8, wherein said pin and said casing are manufactured of brass.

* * * * *